US006489451B1

(12) United States Patent
Li et al.

(10) Patent No.: US 6,489,451 B1
(45) Date of Patent: Dec. 3, 2002

(54) **ANTITHROMBOSIS ENZYME FROM THE SNAKE VENOM OF *AGKISTRODON ACUTUS***

(75) Inventors: Benjamin Xy Li, Ann Arbor, MI (US); Xin Cheng, Anhui (CN)

(73) Assignee: Hefei-Siu-Fung USTC Pharmaceutical Co., Ltd. (CN)

( * ) Notice: Subject to any disclaimer, the term of this patent is extended or adjusted under 35 U.S.C. 154(b) by 0 days.

(21) Appl. No.: 09/058,740

(22) Filed: Apr. 10, 1998

Related U.S. Application Data

(60) Provisional application No. 60/043,886, filed on Apr. 10, 1997.

(51) Int. Cl.$^7$ .......................... C07K 14/00; C12N 9/00; A61K 35/58

(52) U.S. Cl. ...................... 530/856; 530/350; 435/183; 435/219; 424/542; 424/94.1

(58) Field of Search ................................. 530/350, 856; 424/542, 94.1; 435/219, 183

(56) References Cited

U.S. PATENT DOCUMENTS

| | | | |
|---|---|---|---|
| 4,017,012 A | 4/1977 | Brock | 225/96.5 |
| 5,066,592 A | 11/1991 | Huang et al. | 435/240.2 |
| 5,071,773 A | 12/1991 | Evans et al. | 436/501 |
| 5,196,403 A | 3/1993 | Maraganore et al. | 514/12 |
| 5,242,810 A | 9/1993 | Maraganore et al. | 435/69.2 |
| 5,342,830 A | 8/1994 | Scarborough | 514/12 |
| 5,344,783 A | 9/1994 | Scarborough et al. | 436/501 |
| 5,453,370 A | 9/1995 | Triplett et al. | 435/214 |
| 5,523,292 A | 6/1996 | Schwartz et al. | 514/21 |
| 5,686,571 A | 11/1997 | Scarborough et al. | 530/330 |
| 5,733,738 A | 3/1998 | Niman | 435/7.23 |

FOREIGN PATENT DOCUMENTS

| | | |
|---|---|---|
| CN | 92102645.5 | 10/1992 |
| WO | 89/04489 | 5/1989 |
| WO | 91/12258 | 8/1991 |
| WO | 93/09236 | 5/1993 |

OTHER PUBLICATIONS

Atoda et al. Blood Coagulation Factor IX– Binding Protein from the Venom of Trimeresurus flavoviridis: Purification and Characterization. J. Biochem. 118(5): 965–973, 1995.*
Robyt, J.F. "Biochemical Techniques: Theory and Practice", Waveland Press, Prostpect Heights, IL, 1987 p. 300.*
Bajwa et al., "Fibrinolytic enzyme(s) in western diamondback rattlesnake (crotalus atrox) venom," *Toxicon* 18:285–290 (1980).
Bayer et al., "The Avidin–Biotin Complex in Affinity Cytochemistry," *Methods in Enzymology* 62:308–319 (1979).
Bullock et al., "Techniques in Immunocytochemistry," Academic Press, Orlando, FL: vol. 1 (1982), vol. 2 (1983), vol. 3 (1985) (Table of Contents Only).

Campbell, *Monoclonal Antibody Technology: Laboratory Techniques in Biochemistry and Molecular Biology*, vol. 13, Elsevier Science Publishers, Amsterdam, The Netherlands (1984) (Table of Contents Only).
Capecchi, "High Efficiency Transformation by Direct Microinjection of DNA into Cultured Mammalian Cells," *Cell* 22:479–488 (1980).
Chard, *An Introduction to Radioimmunoassay and Related Techniques*, Elsevier Science Publishers, Amsterdam, The Netherlands (1986) (Table of Contents Only).
Chen and Okayama, "High–Efficiency Transformation of Mammalian Cells by Plasmid DNA", *Molecular and Cellular Biology* 7(8):2745–2752 (1987).
Chu et al., "Electroporation for the efficient transfection of mammalian cells with DNA," *Nucleic Acids Research* 15:1311–1326 (1987).
Curiel et al., "Gene Transfer to Respiratory Epithelial Cells via the Receptor–mediated Endocytosis Pathway," *Am. J. Respir. Cell. Mol. Biol.* 6:247–252 (1992).
Dreborg et al., "Ch. 10—The chemistry and standardization of allergens," in *Handbook of Experimental Immunology—vol. 1: Immunochemistry*, 4th Ed., edited by Weir et al., Blackwell Scientific Publications, Oxford, England, pp. 10.1—10.28 (1986).
Engvall and Perlmann, "Enzyme–Linked Immunosorbent Assay, ELISA. III. Quantitation of Specific Antibodies by Enzyme–Labeled Anti–Immunoglobulin in Antigen–Coated Tubes," *J. Immunology* 109:129–135 (1972).
Felgner and Ringold, "Cationic liposome–mediated transfection," *Nature*, 337:387–388 (1989).
Felgner et al., "Lipofection: A Highly Efficient, Lipid–mediated DNA–transfection Procedure," *Proc. Natl. Acad. Sci. USA* 84:7413–7417(1987).
Ferrari et al., "An in Vivo Model of Somatic Cell Gene Therapy for Human Severe Combined Immunodeficiency," *Science* 251:1363–1366 (1991).
Fingl and Woodbury, "Chapter 1—General Principles," in *The Pharmacological Basis of Therapeutics* 5th edition, Goodman and Gilman editors, MacMillan Publishing Co., Inc., New York, pp. 1–46 (1975).
Gennaro (editor), *Remington's Pharmaceutical Sciences* (1990) (Table of Contents Only).
Goding, "Conjugation of Antibodies with Fluorochromes: Modifications to the Standard Methods," *J. Immunological Methods* 13:215–226 (1976).
Hurby et al., "Applications of Synthetic Peptides: Antisense Peptides," in *Synthetic Peptides: A User's Guide*, edited by Gregory A. Grant, W.H. Freeman, NY, pp. 289–307 (1992).

(List continued on next page.)

Primary Examiner—Karen Cochrane Carlson
Assistant Examiner—Rita Mitra
(74) Attorney, Agent, or Firm—Lyon & Lyon LLP

(57) ABSTRACT

This invention features an antithrombosis enzyme extracted and purified from the snake venom of Southern-Anhui *Agkistrodon acutus* and pharmaceutical uses thereof.

13 Claims, 1 Drawing Sheet

OTHER PUBLICATIONS

Kasprzak et al., "Location of a Contact Site Between Actin and Myosin in the Three–Dimensional Structure of the Acto–S1 Complex," *Biochemistry* 28:9230–9238 (1989).

Laemmli, "Cleavage of Structural Proteins during the Assembly of the Head of Bacteriophage T4," *Nature* 227:680–686 (1970).

Lutz et al., "The Distribution of Two hnRNP–Associated Proteins Defined by a Monoclonal Antibody is Altered in Heat–Shocked HeLa Cells," *Experimental Cell Research* 175:109–124 (1988).

Matsuzaki et al., "cDNA cloning of IX/X–PB, a heterogeneous two–chain anticoagulant protein from snake venom," *Biochem. Biophys. Res. Com.* 220(2):382–387 (1996).

Miller, "Human Gene Therapy Comes of Age," *Nature* 357:455–460 (1992).

Morita et al., "Structure and functions of coagulation factor IX/factor x–binding protein isolated from the venom of Trimeresurus flavoviridis," *Natural Toxins II* pp. 187–196 (1996).

Mulligan, "The Basic Science of Gene Therapy," *Science* 260:926–932 (1993).

St. Groth and Scheidegger, "Production of Monoclonal Antibodies: Strategy and Tactics," *J. Immunol. Methods* 35:1–21 (1980).

Sternberger et al., "The Unlabeled Antibody Enzyme Method of Immunohistochemistry: Preparation and Properties of Soluble Antigen–Antibody Complex (Horseradish Peroxidase–Antihorseradish Peroxidase) and its Use in Identification of Spirochetes," *J. Histochemistry and Cytochemistry* 18(5):315–333 (1970).

Tijssen, *Practice and Theory of Enzyme Immunoassays: Laboratory Techniques in Biochemistry and Molecular Biology*, vol. 15, Elsevier Science Publishers, Amsterdam, The Netherlands (1985) (Table of Contents Only).

Wilchek and Jakoby, "The Literature on Affinity Chromatography," *Methods in Enzymology* 34:3–10 (1974).

Yang et al., "In Vivo and In Vitro Gene Transfer to Mammalian Somatic Cells by Particle Bombardment," *Proc. Natl. Acad. Sci. USA* 87:9568–9572 (1990).

\* cited by examiner

CCATGGGGCGATTCATCTTCGTGAGCTTCGGCTTGCTGGTCGTGTTCCTCTCCCTGAGTG    60
[M  G  R  F  I  F  V  S  F  G  L  L  V  V  F  L  S  L  S  G

GAACTGCAGCTGATTGTCCCTCTGAGTGGTCCTCCTATGAAGGGCATTGCTACAAGCCCT   120
 T  A  A] D  C  P  S  E  W  S  S  Y  E  G  H  C  Y  K  P  F

TCGATGAACCTAAGACCTGGGCAGATGCAGAGAAATTCTGCACACAACAACACAAAGGCA   180
 D  E  P  K  T  W  A  D  A  E  K  F  C  T  Q  Q  H  K  G  S

GCCATCTGCCTCTCACAGCAGTGAGAGCGATTGTGT*NNN*...*NNNN*TGGTCACGTTGACC   240
 H  L  P  L  T  A  V  R  A  I  V  *X*  *X* ... *X*  G  H  V  D  H

ACACCAAGTTGAAACTGATTAGTCTGATTGGACTGAAGAACATCTGGAACGGATGCTACT   300
 T  K  L  K  L  I  S  L  I  G  L  K  N  I  W  N  G  C  Y  W

GGAAGTGGAGCGATGGCACCAAGCTCGACTACAAAGACTGGCGTGAACAATTTGAATGTC   360
 K  W  S  D  G  T  K  L  D  Y  K  D  W  R  E  Q  F  E  C  L

TCGTATCCAGGACAGTTAATAACGAATGGCTAAGTATGGACTGCGGCACTACTTGCTCTT   420
 V  S  R  T  V  N  N  E  W  L  S  M  D  C  G  T  T  C  S  F

TCGTCTGCAAGTTCCAGGCATAGTCTGAAGACTA                             454
 V  C  K  F  Q  A  STOP*

Figure 1: Putative cDNA sequence and amino acid sequence of the antithrombosis enzyme, B chain

ANTITHROMBOSIS ENZYME FROM THE SNAKE VENOM OF *AGKISTRODON ACUTUS*

RELATED APPLICATION

This application is converted from provisional application Ser. No. 60/043,886 filed Apr. 10, 1997, the content of which is incorporated by reference herein in its entirety, including claims, sequences and drawings.

FIELD OF THE INVENTION

This invention relates to an antithrombosis enzyme derived from the snake venom of an acutus species.

BACKGROUND OF THE INVENTION

Anti-thrombus drugs extracted from acutus venom have been reported in the literature, e.g., "Preparation and Study of Anti-thrombus Enzymes No. 1, 2, and 3", *Journal of the Medical Univ. of China*, 1989.18 (special issue); and "Technique for Extracting Definriogenase from the venom of *Agkistrodon acutus*," CN 92102645.5 (CN 1065680.A). These anti-thrombus drugs are proteinase components extracted from the snake venom. They act like thrombase with hemorrhagic side-effect. In addition, some of these products are not single component proteinase, but a mixture of different components, which limits the pharmaceutical application of these drugs in human.

Other snake venom derived pharmaceutical products include Ancrod, Trigtamin and Integrilin (see Matsuzaki et al., *Biochem. Biophy. Res. Com.* 220(2):382–387, 1996; Morita et al., *Natural Toxins II*, pp187–196, Edited by B. R. Singh and A. T. Tu, Plenum Press, New York, 1996; U.S. Pat. Nos. 5,196,403, 5,242,810, 5,453,370, 4,017,012, 5,344,783, 5,686,571, 5,523,292, 5,066,592 and 5,342,830).

SUMMARY OF THE INVENTION

Within the scope of this invention, Applicant has extracted, purified and cloned an antithrombosis enzyme (ATE, also called a fibrinolytic enzyme in the provisional application) from the venom of Southern-Anhui *Agkistrodon acutus* in China. This enzyme degrades both fibrinogen and fibrin, and inhibits platelet aggregation. It is useful for preventing and treating vaso-occulusive and thromboembolic disorders, including, but not limited to, myocardial infarction, restenosis, peripheral anginaphraxis, angiopathic thrombosis, cerebral thrombosis, ischemic cerebral vascular diseases, unstable angina, acute thrombosis, unstable stenocardia and hemiparalysis caused by cerebral thrombosis.

The present invention provides methods and compositions for preventing or treating diseases and processes mediated (caused or aggravated) by undesired and/or uncontrolled thrombosis by administering to a human or animal a composition containing or capable of expressing the antithrombosis enzyme in a dosage sufficient to prevent, reduce, eliminate or inhibit thrombosis. The antithrombosis enzyme may be substantially purified or in a crude extract. The antithrombosis enzyme may be produced from snake venom, chemically synthesized or expressed from a recombinant vector. It may also be combined with a pharmaceutically acceptable excipient or carrier, and optionally sustained-release compounds or compositions, such as biodegradable polymers, to form therapeutic compositions.

The present invention is particularly useful for treating or preventing acute and recurrent cerebral thrombosis, myocardial infarction, restenosis, peripheral anginaphraxis, angiopathic thrombosis, ischemic cerebral vascular thrombosis, unstable angina, unstable stenocardia, and thromboangitis obliterans. Administration of the antithrombosisi enzyme can prevent blood clot formation and reduce, diminish or dissolve blood clot. The antithrombosis enzyme may also be used in combination with other compositions and procedures for the treatment of thrombosis. For example, it may be used in combination with a thrombolytic agent known in the art, which includes, but is not limited to, tissue plasminogen activator purified from natural sources, recombinant tissue plasminogen activator, streptokinase, urokinase, prourokinase, anisolated streptokinase plasminogen activator complex (ASPAC), animal salivary gland plasminogen activators and known, biologically active derivatives of any of the above. In these combination compositions, the antithrombosis enzyme and other thrombolytic agent work in a complementary fashion to dissolve blood clots, resulting in decreased reperfusion times and increased reocclusion times in patients treated with them. The use of the antithrombosis enzyme in the compositions of this invention advantageously allows the administration of a thrombolytic reagent in dosages previously considered too low to result in thrombolytic effects if given alone. This avoids some of the undesirable side effects associated with the use of thrombolytic S agents, such as bleeding complications. The compositions of this invention may also be used before, concurrent with, or after angioplastic or fibrolytic treatment to prevent or treat restenosis.

Thus, in a first aspect, this invention features an isolated, purified or recombinant antithrombosisi enzyme which has (i) a molecular weight of between about 28 kD and about 32 kD when analyzed by polyacrylamide gel electrophoresis, (ii) an aspartic acid content of between about 2% and about 5%, and (iii) a glutamic acid content of between about 2% and about 5%. This enzyme has the ability to hydrolyze fibrin, dissolve thrombus, inhibit platelet aggregation, and inhibit the formation of thrombus.

In a preferred embodiment, the enzyme has fibrinolytic activity of no less than one fibrinolytic activity unit per mg protein. In another preferred embodiment, the enzyme has fibrinolytic activity of between about one and about three fibrinolytic activity units per mg protein. This enzyme specifically hydrolyzes the A ($\alpha$) chain of fibrinogen. This enzyme completely or almost completely inhibits human platelet aggregation induced by agonists such as ADP, Epinephrine, Thrombin and collagen. This enzyme has no detectable hydrolysis effect on casein. The enzyme dissolves arterial and venous thrombus in a mammal, prevent thrombosis, reduce blood viscosity, and improve microcirculation. At the same time, this enzyme has minimum effect on the thromosystem, resulting in little possibility of hemorrhage. This enzyme is different from related enzymes from other Acutus species (e.g., IX/X binding proteins, Matsuzaki et al., *Biochem. Biophy. Res. Com.* 220(2):382–387, 1996; Morita et al., *Natural Toxins II*, pp187–196, Edited by B. R. Singh and A. T. Tu, Plenum Press, New York, 1996) in that this enzyme has both fibrinolytic activity and antiplatelet aggregation activity, and less hemorrhagic activity.

In other preferred embodiments, this enzyme is purified from Southern-Anhui *Agkistrodon acutus*. The enzyme is a heterodimer of A chain and B chain each with a molecular weight of about 14 KD to about 16 KD. The A chain has at its amino end the following sequence Sequence ID No. 3:

Asp-Cys-Ser-Ser-Asp-Trp-Ser-Ser-Tyr-Glu-Gly-His-Cys-Tyr-Lys-Val-Phe-Lys-Gln-Ser-Lys-Thr-Trp-Thr-Asp-Ala-Glu-Ser-Phe-, and the B chain has at its amino end the following sequence Sequence ID No. 4:

Asp-Cys-Pro-Ser-Glu-Trp-Ser-Ser-Tyr-Glu-Gly-Phe-Cys-Tyr-Lys-Pro-Phe-. Preferrably, the A chain and the B chain are linked by one or more disulfide bond.

In other preferred embodiments, this antithrombosis enzyme contains Ca++ and/or has aspartic acid at its amino terminus.

By "isolated" in reference to a polypeptide is meant a polypeptide isolated from a natural source or synthesized. The isolated polypeptides of the present invention are unique in the sense that they are not found in a pure or separated state in nature. Use of the term "isolated" indicates that a naturally occurring amino acid sequence has been removed from its normal cellular environment. Thus, the sequence may be in a cell-free solution or placed in a different cellular environment. The term does not imply that the sequence is the only amino acid chain present, but that it is the predominate sequence present (at least 10–20% more than any other sequence) and is essentially free (about 90–95% pure at least) of non-amino acid material naturally associated with it.

By "enriched" in reference to a polypeptide is meant that the specific amino acid sequence constitutes a significantly higher fraction (2–5 fold) of the total of amino acids present in the cells or solution of interest than in normal or diseased cells or in the cells from which the sequence was taken. This could be caused by a person by preferential reduction in the amount of other amino acids present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term "significantly" here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The amino acid from other sources may, for example, comprise amino acid encoded by a yeast or bacterial genome, or a cloning vector such as pUC19. The term is meant to cover only those situations in which man has intervened to elevate the proportion of the desired amino acid.

By "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

By "recombinant" is meant a polypeptide or enzyme produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature. This invention features recombinant ATE and its fragments obtainable using techniques known to those skilled in the art, including those described in McDonnell et al., U.S. patent application Ser. No. 08/223,943 filed Apr. 6, 1994, Evans et al., U.S. Pat. No. 5,071,773, and PCT application, PCT/US91/00399 filed Jan. 22, 1991 (International Publication No. WO 91/12258), incorporated by reference herein.

In a second aspect, this invention features isolated, purified or recombinant polypeptide fragments of the A chain and the B chain of the antithrombosis enzyme. Preferably, these fragments contain no less than 15, 20, 30 or 40 contiguous amino acid residues from the A or B chain. For example, these fragments may contain no less than 15, 20, 30 or 40 contiguous amino acid residues from SEQ ID NO: 2. Such polypeptide fragments can be synthesized chemically or expressed from recombinant vectors. They are useful for generating monoclonal antibodies which bind to both the polypeptide fragments and the intact antithrombosis enzyme (see U.S. Pat. Nos. 5,733,738, 5,015,571, incorporated by reference herein). Monoclonal antibodies so generated can be attached to solid support and used to purify the antithrombosis enzyme from crude venom extract or cell extract by affinity chromatography.

The recombinant polypeptide fragments of the A chain and the B chain can be expressed from recombinant nucleic acid encoding such polypeptide fragments. For example, polypeptide fragments of the A chain can be expressed from recombinant nucleic acid containing no less than 45, 60, 90 or 120 contiguous nucleotides from SEQ ID NO: 1 or its fully complementary strand of the same length and a promoter effective to initiate transcription of the contiguous nucleotides in a host cell.

In yet another aspect the invention features an isolated, enriched, or purified antibody (e.g., a monoclonal or polyclonal antibody) having specific binding affinity to the antithrombosis enzyme or a fragment thereof. The antibody contains a sequence of amino acids that is able to specifically bind to the antithrombosis enzyme. The antibody may be prepared with techniques known to those skilled in the art, including, but not limited to, those disclosed in Niman, PCT application PCT/US88/03921 (International Publication No. WO 89/04489), incorporated by reference herein. By "specific binding affinity" is meant that the antibody will bind to the ATE in a certain detectable amount but will not bind other polypeptides to the same extent under identical conditions.

In another aspect the invention features a hybridoma which produces an antibody having specific binding affinity to the antithrombosis enzyme or a fragment thereof. By "hybridoma" is meant an immortalized cell line which is capable of secreting an antibody.

In another aspect, the invention features an isolated, purified, enriched or purified recombinant nucleic acid encoding the antithrombosis enzyme, a chain of the enzyme, or fragments of the A chain or B chain. For example, the recombinant nucleic acid contains a sequence contiguously encoding SEQ ID NO: 2 and a promoter effective to initiate transcription of the conding sequence in a host cell. In particular, the recombinant nucleic acid contains SEQ ID NO: 1 operably linked to a promoter.

By "isolated" in reference to nucleic acid is meant DNA or RNA isolated from a natural source or synthesized. The isolated nucleic acid of the present invention is unique in the sense that it is not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only nucleotide chain present, but does indicate that it is the predominate sequence present (at least 10–20% more than any other nucleotide sequence) and is essentially free (about 90–95% pure at least) of non-nucleotide material naturally associated with it. Therefore, the term does not encompass an isolated chromosome encoding the ATE.

By "purified" in reference to nucleic acid does not require absolute purity (such as a homogeneous preparation);

instead, it represents an indication that the sequence is relatively purer than in the natural environment (compared to the natural level this level should be at least 2–5 fold greater, e.g., in terms of mg/ml). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

By "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased in a useful manner and preferably separate from a sequence library. The term "significantly" here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The DNA from other sources may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

By "recombinant" in reference to a nucleic acid is meant the nucleic acid is produced by recombinant DNA techniques such that it is distinct from a naturally occurring nucleic acid.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The invention also features a nucleic acid probe for the detection of a nucleic acid encoding the antithrombosis enzyme, its A chain or B chain, or fragments thereof. In an example, the nucleic acid probe contains nucleic acid that will hybridize to SEQ ID NO: 1, but not to the nucleic acid sequence of the IX/X-binding protein (Matsuzaki et al., *Biochem. Biophy. Res. Com.* 220(2):382–387, 1996) under high stringency hybridization conditions. By "high stringency hybridization conditions" is meant those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5× Denhardt's solution, sonicated salmon sperm DNA (50 g/ml), 0.1% SDS, and 10% dextran sulfate at 42° C., with washes at 42° C. in 0.2×SSC and 0.1% SDS. Under stringent hybridization conditions only highly complementary nucleic acid sequences hybridize. Preferably, such conditions prevent hybridization of nucleic acids having 1 or 2 mismatches out of 20 contiguous nucleotides.

In another aspect, the invention describes a recombinant cell or tissue containing an exogenous nucleic acid coding for the antithrombosis enzyme, its A chain or B chain, or fragments thereof.

In another aspect, this invention features a pharmaceutical composition for reducing or eliminating thrombosis in a human or animal subject. This composition contains a pharmaceutically effective amount of the antithrombosis enzyme and a pharmaceutically acceptable carrier.

By "pharmaceutically effective amount" is meant an amount of a pharmaceutical compound or composition having a therapeutically relevant effect on thrombosis or diseases or pathological conditions related to thrombosis. A therapeutically relevant effect prevents or relieves to some extent one or more symptoms of thrombosis or diseases or pathological symptoms related to thrombosis in a patient or returns to normal either partially or completely one or more physiological or biochemical parameters associated with or causative of thrombosis or diseases or pathological symptoms related to thrombosis, e.g., reducing or inhibiting thrombosis; curing, reducing, or inhibiting diseases and processes that are mediated by thrombosis.

In another aspect, this invention features a method of reducing or inhibiting thrombosis in a human or animal subject by administering to the subject a pharmaceutically effective amount of the antithrombosis enzyme.

In another aspect, this invention features a method of isolating and/or purifying the antithrombosis enzyme. In this method, a crude extract containing the antithrombosis enzyme, e.g., a crude extract of the snake venom of Southern-Anhui *Agkistrodon acutus*, is dissolved in a buffer and brought into contact with an anion exchange column, the elution sample with fibrinolytic activity and antiplatelet aggregation activity is collected, concentrated and separated by gel permeation chromatography, and the elution sample with fibrinolytic activity and antiplatelet aggregation activity is collected and desalted. This invention features an antithrombosis enzyme isolated by this process.

The present invention also provides recombinant DNA molecules characterized by a DNA sequence encoding the antithrombosis enzyme alone or fused to a DNA sequence which codes for a conventional anti-thrombosis polypeptide. The synthesis of these DNA molecules may be achieved by methods well known in the art. For example, these recombinant DNA molecules may be isolated from an *Agkistrodon acutus* venom gland cDNA library. The synthesis of cDNA libraries and the choice of vector into which the cDNA molecules may be cloned are conventional techniques. The invention also relates to hosts transformed with these recombinant DNA molecules, as well as to the recombinant products expressed by these hosts. And the present invention relates to chemically synthesized antithrombosis enzyme. Such synthetic polypeptides may be prepared by conventional chemical synthesis techniques, for example, synthesis on a solid support.

This invention further relates to pharmaceutically acceptable compositions and combinations, and methods utilizing these natural, recombinant or synthetic antiplatelet polypeptides in the treatment extracorporeal blood.

By "extracorporeal blood" is meant blood that is removed from a patient, subjected to extracorporeal treatment, and returned to the patient in processes such as dialysis, blood filtration or blood bypass during surgery. The term also includes blood products which are stored extracorporeally for eventual administration to a patient. Such products include whole blood, platelet concentrates and other blood fractions in which inhibition of platelet aggregation and platelet release is desired.

Other features and advantages of the invention will be apparent from the following drawing and detailed description of the invention and from the claims.

BRIEF DESCRIPTION OF THE DRAWING

FIG. 1 shows the putative cDNA sequence and amino acid sequence of the antithrombosis enzyme, B chain. A segment of about 10–20 nucleotides in the cDNA clone is being sequenced. A leader peptide Sequence ID No: 5—M G R F I F V S F G L L V V F L S L S G T A A—is cleaved before the assembly of A chain and B chain to form the antithrombosis enzyme.

DETAILED DESCRIPTION OF THE INVENTION

The present invention includes compositions and methods for the treatment of diseases and pathological conditions. These diseases or pathological conditions are mediated by or associated with thrombosis. The compositions of this invention contain an antithrombosis enzyme, which can be isolated from the venom of Southern-Anhui *Agkistrodon acutus*, or synthesized by chemical or biological methods (e.g., cell culture, recombinant gene expression, or peptide synthesis). Recombinant techniques include gene amplification from DNA sources using the polymerase chain reaction (PCR), RNA polymerase based amplification, and gene amplification from RNA sources using reverse transcriptase/PCR.

Purification of the Antithrombosis Enzyme from Snake Venom

The antithrombosis enzyme of this invention was extracted and purified from the venom of Southern-Anhui *Agkistrodon acutus* in China:

(1) Dissolve the crude snake venom in buffer, proceed with centrifugal precipitation and chromatographic separation through an anion exchange column, and collect roughly-isolated fibrinolytic component by elution. The elution is conducted with both a pH linear gradient and a salt linear gradient. The pH linear gradient is from pH 7.5–8.5 to pH 6.0–7.0; and the salt linear gradient is from 0 to 0.5 M. The elution speed is 25–80 ml/hr.

(2) Concentrate this fibrinolytic component and proceed with gel permeation chromatography to get the refined antithrombosis enzyme solution.

(3) Desalt the refined antithrombosis enzyme solution and get the purified antithrombosis enzyme solution.

The above procedure was conducted at about 4–10° C.

The buffer used to dissolve the crude snake venom and the roughly-isolated elute is a Tris-Hcl buffer (e.g. 0.02 M, pH 7.5–8.5 N-(tris-hydroxymethyl)-amino methane-Hydrochloric acid), or a phosphate buffer (e.g. 0.02 M, pH 7.5–8.5 $Na_2HPO_4$-$NaH_2PO_4$).

The anion exchange column contains weak acidic anion exchanger, e.g., DEAE Sephadex A50, or DEAE Sepharose Fast Flow.

The gel permeation chromatography uses a gel for separating substances in the range between about 5 kD and 300 kD, e.g., Sephacryl S-100HR, S-200HR, S-300HR, or Sephadex G75. The buffer used in the gel permeation chromatography is a 0.05–0.30 M sodium chloride (NaCl) solution.

The fibrinolytic component was concentrated by ultrafiltration, blow-drying with cold air, or freeze-drying. The desalting was conducted against distilled water for 1–6 hrs.

The above method for isolating and purifying the antithrombosis enzyme from the venom of *Agkistrodon acutus* is simple, provides high-purity product and shortens the time by processing the pH linear gradient elution and the salt linear gradient elution simultaneously. The shortened purification cycle increases the efficiency of industrial production.

The purification methods of this invention are also useful to isolate proteolytic fragments of the antithrombosis enzyme which retain the biological activity of the intact polypeptide. Such proteolytic fragments may occur naturally or artifactually as a result of the purification process.

The purification procedure is further described by the following three examples:

EXAMPLE 1

(1) Dissolve 3 g Southern-Anhui *Agkistrodon actus* venom in 20 ml 0.02 M pH 8.0 Tris-Hcl buffer. Centrifuge 15 min at 3000 rpm. Collect the supernatant. Resuspend the pellet in 5 ml above buffer and agitate well. Repeat the centrifugation once. Collect the supernatant with the earlier collection. Store at 4° C.

(2) Process the DEAE Sephadex A-50 anion exchanger with alkaline-acid and wash with distilled water to neutrality. Then wash with 0.02 M pH 8.0 Tris-HCl buffer till the eluate's pH reaches 8.0. Keep in boiling-water bath for 2 hrs to remove air bubbles and ensure swelling.

(3) Pack the column with the processed gel from Step (2) when it is cooled to ambient temperature. The column volume is 3×80 $cm^3$. After equilibration, load the supernatant sample from Step (1) and elute with linear gradient buffer. The buffer in the stock bottle is 0.02 M Tris-Hcl, pH 6.3, containing 0.5 M NaCl. The buffer in the gradient bottle is 0.02 M Tris-HCl buffer, pH 8.0. The flow rate is 42 ml/hr. Examine the eluate under UV 280 nm. Collect the eluate 48 hours after the sample is loaded by automatic fraction collector at the rate of 7 ml per tube and 6 tubes per hour.

12 elution peaks are obtained, among which the 6th is the roughly-isolated fibrinolytic component. It is approximately a 120 ml solution containing 300 mg enzyme.

(4) Put the above fibrinolytic component in a dialysis bag. Blow the bag with cold air till its volume is decreased to about 15 ml. Store at 4° C.

(5) Use Sephacryl S0200HR as gel chromatographic medium to pack the gel chromatographic column. The column volume is 2.7×70 cm$^3$. Wash with 0.5 M NaCl solution for 1 hr at the flow rate of 99 ml/hr, then equilibrate with 0.15 M NaCl solution at the flow rate of 18 ml/min. The second elution peak is the refined antithrombosis enzyme solution which contains 170 mg enzyme in 70 ml of solution.

(6) Put the above refined antithrombosis enzyme into a dialysis bag. Dialyze for 3 hrs against distilled water and get 170 mg purified antithrombosis enzyme.

The purified enzyme was tested to have 1 fibrinolytic activity unit per mg protein. It was tested to show an isoelectric point of pH 5.8 and MW of about 30 kD. No hemorrhagic side effect was detected with the enzyme.

EXAMPLE 2

(1) Dissolve 4.5 g Southern-Anhui *Agkistrodon acutus* venom in 0.02 M, pH 7.8 phosphate buffer. The rest is the same as Step (1) of Example 1. Combine the supernatant and store at 4° C.

(2) Same as Step (2) of Example 1.

(3) Pack the column with the processed gel by the above step. Increase the column volume to 1600 ml (4×100 cm$^3$). Keep the other conditions, 460 mg of enzyme was obtained after the chromatography.

(4) Put the roughly-isolated antithrombosis enzyme in a dialysis bag. Blow the bag with cold air till the volume is decreased to about 20 ml.

(5) Use Sephacryl S-300 HR as gel chromatographic medium to pack the chromatographic column. The column volume is 3.1×70 cm$^3$. Wash 1 hr with 0.5 M NaCl at the flow rate of 99 ml/hr and equilibrate with 0.2 M NaCl. Load the concentrated sample onto the column. Elute with 0.20 M NaCl solution at the flow rate of 24 ml/min. The second peak is the refined antithrombosis enzyme solution. Desalt the solution and get 280 mg purified enzyme in 100 ml solution.

EXAMPLE 3

(1) Dissolve 3 g *Agkistrodon acutus* venom as described in Step (1) of Example 1.

(2) Use DEAE Sepharose Fast Flow as the anion exchanger. Process it and pack the column as described in Step (2) of Example 1. The column volume is 3×80 cm$^3$. Rinse the column with 0.02 M pH 8.0 Tris-HCl buffer at the flow rate of 1.5 ml/min till equilibration. Load the sample and elute with a linear gradient. The elution buffer is the same at that in Step (3) of Example 1. Adjust the flow rate to 80 ml/hr. 285 mg of enzyme was collected.

(3) The following procedure is the same as that of Example 1. In the end 160 mg refined antithrombosis enzyme in 60 ml solution was obtained which was shown to have fibrinolytic activity and no hemorrhagic side-effect.

Crystallization of the Antithrombosis Enzyme

The antithrombosis enzyme was obtained as described above (with a purity of 99% or higher) and further desulted. Crystals of the antithrombosis enzyme were grown by hanging-drop vapour diffusion technique using tissue culture plates and silicomised glass coverslips. At room temperature (about 20° C.), 3 µl of protein solution (30 mg/ml, in distilled water) was mixed with an equal volume of precipitant solution (0.1 M Mes buffer, pH 6.5, containing 16% PEG4000 (w/v) and 0.1 M CaAc2). The solution was then equilibrated against 400 µl of precipitant solution containing 20% PEG 4000 (w/v). Crystals were collected from the solution in about one week. These crystals are useful for deciphering the tertiary structure and function center of the enzyme by X-ray crystallography and other techniques Characterization of the Antithrombosis Enzyme The antithrombosis enzyme purified from the snake venom of Southern-Anhui *Agkistrodon acutus* contains $Ca^{++}$. Applicant studied the purity, fibrinolytic characteristic, antiplatelet aggregation activity, amino acid structure, proteolytic activity and hemorrhagic activity of the antithrombosis enzyme.

The activities of the antithrombosis enzyme of the present invention may be assayed in vitro using any conventional technique. Preferably, the anti-thrombin assay involves direct determination of the thrombin-inhibitory activity of the molecule. Such techniques measure the inhibition of thrombin-catalyzed cleavage of calorimetric substrates or the increase in thrombin times or increase in activated partial thromboplastin times of human plasma. Alternatively, the assay employed may use purified thrombin and fibrinogen to measure the inhibition of release of fibrinopeptides.

The antiplatelet activity can be measured through a change in the degree of aggregation of platelets or a change in the release of a platelet secretory component in the presence of platelet activator. The former may be measured in an aggregometer. The latter may be measured using RIA or ELISA techniques specific for the secreted component.

Purity

Polyacrylamide gel electrophoresis of the enzyme as purified above under nonreducing condition showed one band at about 28–30 kD and the purity to be more than 90%.

Components

SDS-polyacrylamide gel electrophoresis was carried out according to the method of Laemmli (*Nature* 227:680–685, 1970). Standards used for molecular weight determination were obtained from Sigma (bovine serum albumin—66 kD, ovalbumin—45 kD, glyceraldehyde-3-phosphate dehydrogenase—36 kD, carbonic anhydrase—29 kD, trypsinogen—24 kD and lactalbumin—14 kD). Staining was done with Coomassie brilliant blue R250.

Two bands were present on the SDS-PAGE gel. Thus the enzyme was isolated into two chains, A chain and B chain, each with a molecular weight of about 14 kD to about 16 kD on SDS-PAGE.

Fibrinolytic Activity

Fibrinolytic activity was measured with the fibrin-plate-clearance assay (Bajwa et al. *Toxicon* 18:285–290, 1980). The positive control and the negative control were plasmin (Sigma) and 0.9% sodium chloride, respectively. The experiment showed that the enzyme has high fibrinolytic activity in comparison to the control and the size of lysis area on the plate was proportional to the enzyme dosage. The enzyme was measured to hydrolyze fibrin at the level of about one to about three fibrinolytic activity units per mg of enzyme.

Fibrinogen Cleavage Sites

Fibrinogen was incubated with the antithrombosis enzyme to determine the initial cleavage sites. Fibrinogen (30 nmol) was dissolved in 2 ml of 0.05 M Tris buffer, pH 8.0. 10 µl of the antithrombosis enzyme (0.6 nmol) was added to this solution. The solution was incubated at 37° C. for 1 hr. The reaction was stopped by the addition of 1 ml of 250 mM EDTA. This incubation time was employed as being optional for the accumulation of early degradation products.

The solution was then brought to 8 M Urea. Degraded fibrinogen fragments were reduced by the addition of dithiothreitol in a 10-fold molar excess over fibrinogen.

The sample was added to a $C_{18}$ reversed phase chromatography column for separation. Five fragments were collected and freeze-dried. The amino-terminal amino acid sequences (1–10 residues) were determined. One fibrinogen cleavage site was found to be Met 235-Pro236 of the α chain of human fibrinogen. Other cleavage sites are still being studied.

Antiplatelet Aggregation Activity

ADP, collagen, epinephrine bitartrate and thrombin were obtained from Sigma Chemical Co. (St. Louis, Mo.). Venous blood was collected from healthy human donors who were drug-free and aspirin-free for at least 2 weeks before blood collection. Blood was collected into cirated Vacutainer tubes and centrifuged for 15 minutes at 150 g at room temperature. The platelet-rich plasma (PRP) was removed. The remaining blood was centrifuged for 15 minutes at 1500 g at room temperature, and the platelet-poor plasma (PPP) was removed.

Samples were assayed on a TYSM-91 Platelet Aggregometer with PPP as the blank (100% transmittance). PRP (200 µl, $5\times10^8$ platelets/ml) was added to each micro test tube, and transmittance was set at 0%.

A stimulator of platelet aggregation such as ADP (200 µl, 10 µmol/l), collagen, epinephrine bitartrate or thrombin was added to a tube, and the aggregation profiles were plotted (percent transmittance versus time). The antithrombosis enzyme (20 µl) of varying concentrations was added to the test tube before the addition of the platelet agonist. Antiplatelet aggregation activity is expressed as percent inhibition of agonist-induced platelet aggregation.

It was shown that the antithrombosis enzyme inhibits human platelet aggregation induced by ADP, Epinephrine, thrombin and collagen.

Primary Structure

The amino acid sequences of the A chain and the N-terminal of the B chain have been determined:

A Sequence ID No: 2: Asp-Cys-Ser-Ser-Asp-Trp-Ser-Ser-Tyr-Glu-Gly-His-Cys-Tyr-Lys-Val-Phe-Lys-Gln-Ser-Lys-Thr-Trp-Thr-Asp-Ala-Glu-Ser-Phe-Cys-Thr-Lys-Gln-Val-Asn-Gly-Gly-His-Leu-Val-Ser-Ile-Glu-Ser-Ser-Gly-Glu-Ala-Asp-Phe-Val-Gly-Gln-Leu-Ile-Ala-Gln-Lys-Ile-Lys-Ser-Ala-Lys-Ile-His-Val-Trp-Ile-Gly-Leu-Arg-Ala-Gln-Asn-Lys-Glu-Lys-Gln-Cys-Ser-Ile-Glu-Trp-Ser-Asp-Gly-Ser-Ser-Ile-Ser-Lys-Glu-Asn-Trp-Ile-Glu-Glu-Glu-Ser-Lys-Lys-Cys-Leu-Gly-Val-His-Ile-Glu-Thr-Gly-Phe-His-Lys-Trp-Glu-Asn-Phe-Tyr-Cys-Glu-Gln-Gln-Asp-Pro-Phe-Val-Cys-Glu-Ala B Sequence ID No: 4: N-Asp-Cys-Pro-Ser-Glu-Trp-Ser-Ser-Tyr-Glu-Gly-Phe-Cys-Tyr-Lys-Pro-Phe- The amino acid sequence of the A chain was determined by a combination of deduction from the cDNA sequence and amino acid sequencing of the N-terminal of purified A chain.

FIG. 1 shows the putative amino acid sequence of the entire B chain, including a leader peptide, i.e. Sequence ID No: 5, M G R F I F V S F G L L V V F L S L S G T A A, which is cleaved before the assembly of A chain and B chain to form the antithrombosis enzyme.

Proteolytic Activity

The proteolytic activity of the antithrombosis enzyme was assessed by azocasein hydrolysis. Azocasein was synthesized from casein and diazotised sulfanilamide. The resulting azocasein solution in 1% sodium bicarbonate had a concentration of 42 mg/ml. 1 ml of the azocasein solution was added to a tube. A solution of the antithrombosis enzyme was added, and the tube was incubated at 37° C. for 30 minutes. The perchloric acid was added into the tube, and the resulting precipitate was removed by centrifugation. Hydrolysis of azocasein was measured by increased absorbance at 390 nm of the supernatant. No proteolytic activity was detected in this assay.

Hemorrhagic Activity

The antithrombosis enzyme (100–200 µg) was injected subdermally under the clean shaven backs of white mice. After 24 hours, the mice were sacrificed and their skin observed for hemorrhage. No hemorrhage on the skin was observed after the administration of the antithrombosis enzyme.

Pharmacology of the Antithrombosis Enzyme in Animal Studies

Effect on Thrombosis

The antithrombosis enzyme was administered to rabbits intravenously. Thrombosis was determined before the administration and after the administration at 0.5, 1.0, 2.0, and 3.0 hours by the Chandler method. The enzyme showed anti-thrombosis activity at 0.5 hr following administration at 0.005 u/kg and this activity was increased significantly at 1.0 hr and at 0.01 u/kg.

Effect on Arteria Thrombus and Venous Thrombus

Rats were anesthetized and their abdominal aorta and abdominal vein were exposed after surgery. Threads were passed through the abdominal aorta and abdominal vein. After two hours, the antithrombosis enzyme was injected from the femoral vein. Four hours later, the threads were taken out to observe the arteria thrombus and the venous thrombus on the thread. The enzyme was shown to dissolve the arteria thrombus and the venous thrombus starting at 0.025 u/kg and effectively at 0.05 u/kg.

Effect on Pulmonary Thrombus

Pulmonary thrombus was detected and measured with $^{125}$I labeled fibrinogen. The radiation strength in the blood was determined with isotope counting method after the administration of the enzyme intravenously. The enzyme was shown to dissolve pulmonary thrombus in rats effectively at 0.005, 0.01, and 0.02 u/kg.

Effect on Fibrinogen

The enzyme was administered to rabbits intravenously. The content of fibrinogen in the plasma was determined at different times after administration. The enzyme was shown to reduce the fibrinogen content in the blood at 0.0025 u/kg, 0.005 u/kg, and 0.01 u/kg.

Effect on Platelet Aggregation

Dogs were anesthetized and placed on a respiratory pump with the stroke volume adjusted according to the dog's weight. The respirator dials were set to 20 beats per minute and 50% respiration. Both femoral arteries were cannulated, one was attached to a transducer by which the heart beat and blood pressure were monitored on a chart recorder throughout the test, and the other was used for repeated blooding sampling. The formal vein was also cannulated to administer antithrombosis enzyme or vehicle and for the maintenance of anesthesia as needed.

Animals were dosed intravenously with antithrombosis enzyme at different dosage levels. Bleeding time and platelet aggregation were determined before and at different intervals after the administration of the antithrombosis enzyme. Aspirine (35 mg/kg) was used as the positive control and 0.9% sodium cloride was used as the negative control.

It was shown that the antithrombosis enzyme prolongs the blooding time and inhibits platelet aggregation.

Effect on ELT

The enzyme was administered to rabbits intravenously. ELT in the blood of the rabbits was determined at different times after administration. The enzyme was shown to shorten ELT effectively starting at about 120 minutes from administration.

Effect on the Content of FDP in the Blood

The enzyme was administered to rabbits intravenously. The content of FDP in the blood of the rabbits was determined at different times after administration. The enzyme was shown to increase the content of FDP in the blood significantly in a dosage dependent manner.

Effect on The Whole Blood Clotting Time

The enzyme was administered to rabbits intravenously. The whole blood clotting time (CT) was determined. Two hours following the administration, the enzyme showed anti-clotting activity.

Effect on the Kaolin Partial Thromboplastin Time

The enzyme was administered to rabbits intravenously. The KPTT was determined. 240 minutes following the administration, the enzyme was shown to prolong the KPTT significantly.

Effect on Thrombin Time

The enzyme was administered to rabbits intravenously. The TT was determined at the different time after administration. 240 minutes following the administration, the enzyme was shown to prolong the TT significantly.

Effect on Blood Viscosity

The enzyme was administered to rabbits intravenously. The blood viscosity was determined at different times after administration. 120–240 minutes following the administration, the enzyme was shown to reduce the blood viscosity significantly.

General Pharmacology

Dogs were anesthetized with pentobarbital sodium (30 mg/kg). The antithrombosis enzyme at dosages in the range of 0.0015–0.06 u/kg was administrated intravenously. The left arteria carotis was isolated. The aortic systolic pressure, diastolic pressure, mean pressure and heart rate were recorded directly by TP-200T pressure transducer and RM-6000 multi-channel physiological recorder. At the same time, the respiratory curve and the electrocardiogram were recorded. The enzyme did not show significant effects on the above parameters.

When the enzyme was administered to mice intravenously from the tail, it did not affect the behavior of the mice. The enzyme did not activate or restrain the neural system of the mice.

Pharmacokinetics

The pharmacokinetics of the enzyme in the rats was studied with $^{125}$I labeled antithrombosis enzyme at 0.02, 0.01, and 0.005 u/kg. The Concentration-Time Curves of the enzyme in the blood were very similar at the three dosages which is in agreement with the Two-Room Model. $T_{1/2}$ is 6 hours. Among organs, the enzyme distributes mainly in the lung and the kidney. The enzyme can infiltrate through the blood-brain-barrier. It is excreted mainly through urine.

Cloning and Expression of the Antithrombosis Enzyme

A wide variety of methods may be used in locating and identifying cDNA sequences corresponding to A chain and B chain of this invention. The two most preferred techniques are the use of oligonucleotide probe based on the amino acid sequences of A chain and B chain and immunoscreening, which utilizes antibodies against A chain or B chain to detect clones which express cDNA sequences corresponding to the polypeptide.

The immuno screening technique requires that the cDNA library be contained in an expression vector. Such vectors include lambda gt11, lambda gt10 and other expression vectors known in the art. Antibodies employed in the immunoscreening technique include antibodies against the intact antithrombosis enzyme of the present invention, antibodies against denatured polypeptide and antibodies against peptide portions of the antithrombosis enzyme. Once a cDNA clone has been identified and isolated, it may be removed from the vector and analyzed to determine whether it contains the entire antithrombosis enzyme coding sequence. Partial cDNAs may themselves be used to reprobe the cDNA library and to locate full-length cDNAs.

The DNA molecules of this invention may be synthesized from oligonucleotides by chemical means using an oligonucleotide synthesizer. Such oligonucleotides may be designed based on the disclosed amino acid sequences of the antithrombosis enzyme.

Standard methods may be applied to synthesize a gene encoding the antithrombosis enzyme with knowledge of the enzyme's amino acid sequence. For example, the complete amino acid sequence may be used to construct a back-translated gene. A DNA oligomer containing a nucleotide sequence capable of coding for the desired antithrombosis enzyme may be synthesized in a single step. Alternatively, several smaller oligonucleotides coding for portions of the antithrombosis enzyme may be synthesized and subsequently ligated together. Preferably, the antithrombosis enzyme gene is synthesized as 10–20 separate oligonucleotides which are subsequently linked together. The individual oligonucleotides contain 5' or 3' overhangs for complementary assembly.

Following synthesis of the oligomers and cleavage of the desired vector, assembly of the antithrombosis enzyme gene may be achieved in one or more steps by techniques well known in the art. Once assembled, the gene will be characterized by sequences which are recognized by restriction endonucleases, including unique restriction sites for direct assembly into a cloning or an expression vector; preferential condons based upon the host expression system to be used: and a sequence which, when transcribed, produces a mRNA with minimal secondary structure. Proper assembly maybe confirmed by nucleotide sequencing, restriction mapping, and expression of a biologically active antithrombosis enzyme in a suitable host.

It will be understood by those of skill in the art that, due to the degeneracy of the genetic code, many different synthetic DNAs will be capable of encoding the antithrombosis enzyme of this invention. It will also be apparent that many of these DNAs will be faithfully expressed in host transformed with them. Therefore, the present invention relates to not only one, but all DNA molecules which encode the desired antithrombosis enzyme and which can be expressed by one or more hosts transformed with them. Most of these DNA molecules will be capable of hybridizing to one another under moderately stringent conditions.

The DNA sequences and recombinant DNA molecules of the present invention may be inserted into and expressed using a wide variety of vectors. As such, the DNA sequence encoding the antithrombosis enzyme of the invention must be operatively linked to an expression control sequence. The term "operatively linked", as used herein refers to a positioning in a vector so that transcription and translation of the coding sequence is directed by the control sequence. Useful vectors may consist of segments of chromosomal, non-chromosomal and synthetic DNA sequences, such as various known derivatives of SV40, bovine papilloma virus, adenovirus and cytomegalovirus and known bacterial plasmids, e.g., plasmids from E. coli including colEl, pCRl, pBR322, pMB9 and RP4; phage DNAs, e.g., the numerous derivatives of lambda phage, e.g., NM 989, and other DNA phages, e.g., M13 and other Filamentous single-stranded DNA phages; vectors useful in yeasts, such as the 2 μm plasmid; vectors useful in animal cells, such as those containing SV40 adenovirus and retrovirus-derived DNA sequences; commercially available high expression vectors, e.g., the pGEM series and the lambda Zap vectors; and vectors derived from combinations of plasmids and phage DNAs, such as plasmids which have been modified to employ phage DNA or other derivatives thereof.

Such expression vectors are also characterized by at least one expression control sequence. When the DNA sequences of this invention are inserted in the vector they should be operatively linked to such expression control sequence in order to control and to regulate the expression of that cloned DNA sequence. Examples of useful expression control sequences include the malE system, the OmpA system, the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast-mating factors, and promoters derived from polyoma, adenovirus, retrovirus, and simian virus, e.g., the early and late promoters of SV40, and other sequences known to control the expression of genes of prokaryotic or eukaryotic cells and their viruses or combinations thereof.

Furthermore, within each specific expression vector, various sites may be selected for insertion of DNA sequences encoding the antithrombosis enzyme or a fusion protein of this invention. These sites are usually designated by the restriction endonuclease which cuts them. They are well recognized by those of skill in the art. It is, of course, to be understood that an expression vector useful in this invention need not have a restriction endonuclease site for insertion of the chosen DNA fragment. Instead, the vector may be joined to the fragment by alternative means.

The expression vector, and in particular the site chosen therein for insertion of a selected DNA fragment and its operative linking therein to an expression control sequence, is determined by a variety of factors, e.g., number of sites susceptible to a particular restriction enzyme, size of the protein to expressed, susceptibility of the desired protein to proteolytic degradation by host cell enzymes, contamination or binding of the protein to be expressed by host cell proteins difficult to remove during purification, expression characteristics, such as the location of start and stop codons relative to the vector sequences, and other factors recognized by those of skill in the art. The choice of a vector and an insertion site for a DNA sequence is determined by a balance of these factors, not all selections being equally effective for a given case.

Useful hosts which may be transformed with these vectors and which may be employed to express the polypeptides of this invention may include well known eukaryotic and prokaryotic hosts, such as strains of E. coli, such as E. coli SG-936, E. coli HB 101, E. coli W3110, E. coli X1776, E. coli X2282, E. coli DHI, and E. coli MRCl, Pseudomonas, Bacillus, such as bacillus subtilis, Streptomyces, yeasts and other fungi, animal cells, such as COS cells and CHO cells, human cells, insect cells and plant cells in tissue culture.

Of course, not all host/expression vector combinations will function with equal efficiency in expressing the DNA sequences of this invention or in producing the antithrombosis enzyme or fusion polypeptide. However, a particular selection of a host-expression vector combination may be made by those of skill in the art, after due consideration of the principles set forth herein without departing from the scope of this invention. For example, the selection should be based on a balancing of a number of factors. These include, for example, compatibility of the host and vector, toxicity of the proteins encoded by the DNA sequence to the host, ease of recovery of the desired protein, expression characteristics of the DNA sequences and the expression control sequences operatively linked to them, biosafety, costs and the folding, form or any other necessary post-expression modifications of the desired protein.

Constructing a λ cDNA Library from the Venom Gland

After three days of venom extraction, Agkistrodon acutus snakes were sacrificed by decapitation. The venom gland was collected and immediently frozen in liquid nitrogen. Total RNA was extracted from the venom gland with isothiocyanate-phenol-chloride. mRNA was purified from the total RNA by an oligo(dT)-cellulose column. The first DNA strand was synthesized by reverse transcriptase. The second DNA strand was then synthesized and EcoRI adapters were ligated to the ends of the cDNA. This cDNA was ligated into λ gt11 vector and packaged. The packaged DNA was titered and found to contain $1.1 \times 10^6$ recombinants. Finally, $1.7 \times 10^{10}$ pfu/ml were amplified to make the cDNA library.

Primers for cDNA Amplification of the Antithrombosis Polypeptides

One forward primer PF2 was designed according to the N-terminal amino acid sequence of the A chain. PF2 Sequence ID No: 6: Y E G H C Y Sequence ID No: 7, 5' TATGAAGGGCATTGCTACAA 3'

Another forward primer was designed from the 5'-terminal of the cDNA sequence of IX/X-Binding Protein containing the start codon (ATG) Sequence ID No: 8: PF3: 5' CCATGGGGCGATTCATCTTC 3'

A reverse primer (PR1) was designed from the 3'-terminal of the cDNA sequence of the IX/X-Binding Protein containing the stop codon (TGA) Sequence ID No: 9. PR1: 5' CAGCTGCATCTTCAGACTA 3'

The λ gt11 Forward Primer and Reverse Primer were also used to amplify the λ cDNA. λ gt11 Forward Primer Sequence ID No: 10: 5' GGTGGCGACGACTCCTG-GAGCCCG 3' λ gt11 Reverse Primer Sequence ID No: 11: 5' TTGACACCAGACCAACTGGTAATG 3'

Amplification of Clones Encoding the Antithrombosis Polypeptides

The λ cDNA library was used as the template for PCR amplification. The PCR products were analyzed by 1.5% agarose gel electrophoresis and purified from low temperature melting gel. The PCR products were treated with Klenow fragment to generate blunt-ended DNA and inserted into the pBluscript vector at the SmaI site with the T4 DNA ligase. Fresh competent *E. coli* was transformed with the ligation solution and positive colonies were selected by color. The positive clones were digested with HindIII/BamHI and sequenced with T3 and T7 primers and the T7 sequencing Kit (Promega).

One of the clones amplified with PF2/poly(T) primers, Clone A, contains 544 bp as shwon in SEQ ID NO: 1 which encodes the A chain of the antithrombosis enzyme from EGHCY to the carboxyl end.

One of the clone amplified with PF3/PR1 primers, Clone B, contains about 500 bp as shown in FIG. 1 which putatively encodes the B chain of the antithrombosis enzyme.

The λ cDNA library was further screened with clone A as the probe. Several positive clones with inserts ranging from 500 bp to 1.2 kb have been selected to be sequenced.

Pharmaceutical Indications

Pathogenic platelet aggregation may yield thrombi (blood clots) which occlude blood flow to dependent tissues and lead to a variety of life-threatening vascular diseases, such as myocardial infarction, stroke, pulmonary embolism, deep vein thrombosis, peripheral arterial occlusion and other blood system thromboses. Methods of preventing or inhibiting platelet aggregation and release are desirable in the treatment of these diseases. Inhibition of platelet aggregation may also be desirable in dialysis, storage of platelets in platelet concentrates, and following vascular surgery such as angioplasty.

The antithrombosis enzyme of this invention is effective for the treatment of thrombotic diseases, including, but not limited to, angiopathic thrombosis, cerebral thrombosis, acute thrombosis, peripheral anginaphraxis, ischemic cerebral vascular disease, unstable angina, unstable stenocardia, hemiparalysis caused by cerebral thrombosis, myocardial infarction, stroke, pulmonary embolism, deep vein thrombosis and peripheral arterial occlusion; restenosis following arterial injury or invasive cardiological procedures; acute or chronic atherosclerosis; edema and inflammation; abnormal cell regulatory processes (e.g. secretion, shape changes, proliferation); cancer and metastasis; and neurodegenerative diseases. It may also used during the recovery period of cerebral hemorrhage to reduce or inhibit blood clot in the brain.

Toxicology Studies

Acute Toxicity

The acute toxicity of the antithrombosis enzyme was studied with rats and mice and two injection routes (i.t.v. and i.p.). The results are shown below:

TABLE 1

| animal | injection routes | LD$_{50}$(95% reliability) |
| --- | --- | --- |
| mouse | i.t.v. | 14.1 u/kg (9.7~17.5 u/kg) |
|  | i.p. | 23.3 u/kg (18.4~29.5 u/kg) |
| rat | i.t.v. | 14.1 u/kg (22.2~17.2 u/kg) |
|  | i.p. | 14.1 u/kg (46.7~63.5 u/kg) |

Long-term Toxicity

For 8 weeks, rats were given the enzyme (i.t.v.) at dosages pharmaceutically equivalent to 12.5, 50, 200 times that's used clinically for adult humans. Neither abnormal behavior nor toxic symptom was observed. The consumption of food and water, net weight increase, various biochemical indexes and coefficients of major organs and tissues showed no visible change among the testing groups. Pathological histology examination of major organs did not show distinct toxicosis pathology changes.

Side Effects & Contra-indications:

The enzyme has no neural toxicity and is non-hemorrhagic. No obvious side effects have been noticed in clinical use.

The antithrombosis Enzyme Polypeptides, Antibodies and Hybridomas

A variety of methodologies known in the art can be utilized to obtain the polypeptide of the present invention. The polypeptide may be purified from a snake which naturally produces the polypeptide, chemically synthesized, or expressed by recombinant techniques.

Any eukaryotic organism can be used as a source for the polypeptide of the invention, as long as the source organism expresses such a polypeptide. One skilled in the art can readily follow known methods for isolating proteins in order to obtain the polypeptide free of natural contaminants. These include, but are not limited to: size-exclusion chromatography, HPLC, ion-exchange chromatography, and immuno-affinity chromatography.

The present invention relates to an antibody having binding affinity to the antithrombosis enzyme polypeptide. The present invention also relates to an antibody having specific binding affinity to the antithrombosis enzyme polypeptide. Such an antibody may be isolated by comparing its binding affinity to the antithrombosis enzyme polypeptide with its binding affinity to another polypeptide. Those which bind selectively to the antithrombosis enzyme would be chosen for use in methods requiring a distinction between the antithrombosis enzyme and other polypeptides.

The antithrombosis enzyme polypeptide of the present invention can be used in a variety of procedures and methods, such as for the generation of antibodies, for use in identifying pharmaceutical compositions, and for studying DNA/protein interaction.

The antithrombosis enzyme polypeptide of the present invention can be used to produce antibodies or hybridomas. One skilled in the art will recognize that if an antibody is desired, such a peptide would be generated as described herein and used as an immunogen. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, *Monoclonal Antibody Technology: Laboratory Techniques in Biochemistry and Molecular Biology*, Elsevier Science Publishers, Amsterdam, The Netherlands (1984); St. Groth et al., *J. Immunol. Methods* 35:1–21(1980)). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)). Hybridomas secreting the desired antibodies are cloned and the class and subclass is determined using procedures known in the art (Campbell, *Monoclonal Antibody Technology: Laboratory Techniques in Biochemistry and Molecular Biology*, supra (1984)).

For polyclonal antibodies, antibody containing antisera are isolated from the immunized animal and screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315(1970); Bayer et at., *Meth. Enzym.* 62:308(1979); Engval et al., *Immunot.* 109:129(1972); Goding, *J. Immunol. Meth.* 13:215(1976)). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., *Handbook of Experimental Immunology* 4th Ed., Blackwell Scientific Publications, Oxford, England, Chapter 10(1986); Jacoby et al., *Meth. Enzym.* 34 Academic Press, N.Y. (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., *Application of Synthetic Peptides: Antisense Peptides*, In Synthetic Peptides, A User's Guide, W. H. Freeman, N Y, pp. 289–307 (1992), and Kaspczak et al., *Biochemistry* 28:9230–8(1989).

The present invention encompasses a method of detecting the antithrombosis enzyme polypeptide in a sample, comprising: a) contacting the sample with an above-described antibody, under conditions such that immunocomplexes form, and b) detecting the presence of said antibody bound to the polypeptide. In detail, the methods comprise incubating a test sample with one or more of the antibodies of the present invention and assaying whether the antibody binds to the test sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *An Introduction to Radioimmunoassay and Related Techniques* Elsevier Science Publishers, Amsterdam, The Netherlands (1986); Bullock et al., *Techniques in Immunocytochemistry*, Academic Press, Orlando, Fla. Vol. 1(1982), Vol. 2 (1983), Vol. 3 (1985); Tijssen, *Practice and Theory of Enzyme Immunoassays: Laboratory Techniques in Biochemistry and Molecular Biology*, Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily adapted in order to obtain a sample which is capable with the system utilized.

This invention relates to a kit containing all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

Pharmaceutical Formulations and Modes of Administration

The antithrombosis enzyme of the present invention may be formulated into pharmaceutically acceptable compositions for inhibiting both thrombin- and platelet mediated functions in a patient or in extracorporeal blood.

The dosage and dose rate of the antithrombosis enzyme of this invention will depend on a variety of factors, such as the patient's body weight, the specific pharmaceutical composition used, and the object of the treatment, i.e., therapy or prophylaxis, the nature of the thrombotic disease to be treated, and the judgment of the treating physician. A pharmaceutically effective amount of the antithrombosis enzyme of this invention will normally be in the dosage range of between about 0.001–500 mg/kg body weight, preferably about 0.1–50 mg/kg body weight. For the treatment of extracorporeal blood,the antithrombosis enzyme should be used at about 0.005–50 μg/ml, preferably at about 0.5–5 μg/ml of extracorporeal blood. It should be understood that other dosages outside of these illustrative ranges may be employed in the pharmaceutical compositions of this invention.

The antithrombosis enzyme that affects the disorders of interest can be administered in pharmaceutically acceptable formulations where it is mixed with suitable carriers or excipient(s). These formulations can be administered by standard routes, including, but not limited to, intracerebroventricular, intracerebral, intravaginal, intrauterine or parenteral (e.g., intravenous, intraspinal, subcutaneous or intramuscular) route.

In treating a patient exhibiting a disorder of interest, a therapeutically effective amount of a agent or agents is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The dosage of the antithrombosis enzyme will depend on the disease state or condition being treated and other clinical factors such as weight and condition of the patient and the route of administration of the compound. It is to be understood that the present invention has application for both human and veterinary use. The present invention contemplates single as well as multiple administrations, given either simultaneously or over an extended period of time.

The exact formulation, route of administration and dosage can be chosen by the individual physician in view of the patient's condition. (See e. Fingl et al., in *The Pharmacological Basis of Therapeutics*, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include intestinal administration or parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Dosage & Parental Administration

The antithrombosis enzyme could be administered to patients by intravenous injection. The enzyme is supplied as sterile lyophilized white powder in vials. Each vial contains 0.25 unit. For treatment, dissolve this drug aseptically by adding proper sterile water. The solution is diluted with 250 ml of 0.9% Sodium Chloride and is given intravenously at the rate of 45 drops/min. 0.25 unit is given per day.

For acute treatment 0.5 u is given on the first day and 0.25 u/day afterwards. The course of treatment is two weeks.

The drug should be administered under the supervision of a physician.

Perform intradermal test before administration. The drug is diluted into 0.0025 u/ml. Take 0.1 ml and inject intradermally. Observe the result after 20 min. The drug should not be given to the patient if the test result is positive.

Platelet count should be checked in regular intervals (once a week). If the platelet count falls below 80,000/mm$^3$, the treatment should be discontinued immediately.

Gene Therapy with the ATE

The antithrombosis enzyme or its genetic sequences will be useful in gene therapy (reviewed in Miller, *Nature* 357:455–460, 1992). Miller states that advances have resulted in practical approaches to human gene therapy that have demonstrated positive initial results. An in vivo model of gene therapy for human severe combined immunodeficiency is described in Ferrari, et al., *Science* 251:1363–1366, (1991). The basic science of gene therapy is described in Mulligan, *Science* 260:926–931, (1993).

In one preferred embodiment, one or more expression vector containing the ATE coding sequence is inserted into cells, the cells are grown in vitro and then infused in large numbers into patients.

The gene therapy may involve the use of an adenovirus containing ATE cDNA targeted to a vascular tissue, systemic ATE increase by implantation of engineered cells, or injection of naked ATE DNA into appropriate tissues.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant ATE polypeptides into the targeted cell population (e.g., tumor cells). Methods which are well known to those skilled in the art can be used to construct recombinant viral vectors containing coding sequences. See, for example, the techniques described in Maniatis et al., *Molecular Cloning: A Laboratory Manual*, Cold Spring Harbor Laboratory, N.Y. (1989), and in Ausubel et al., *Current Protocols in Molecular Biology*, Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., *Nature* 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. Capecchi M R, *Cell* 22:479–88 (1980). Once recombinant genes are introduced into a cell, they can be recognized by the cell's normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, *Mol. Cell Biol.* 7:2745–52 (1987)); electroporation, wherein cells are exposed to large voltage pulses to introduce holes into the membrane (Chu G. et al., *Nucleic Acids Res.*, 15:1311–26 (1987)); lipofection/liposome fusion, wherein DNA is packaged into lipophilic vesicles which fuse with a target cell (Felgner P L., et al., *Proc. Natl. Acad. Sci. USA*. 84:7413–7 (1987)); and particle bombardment using DNA bound to small projectiles (Yang N S. et al., *Proc. Natl. Acad. Sci.* 87:9568–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel D T et al., *Am. J. Respir. Cell. Mol. Biol.*, 6:247–52 (1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding ATE is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

All publications referenced are incorporated by reference herein, including the nucleic acid sequences and amino acid sequences listed in each publication.

Other embodiments of this invention are disclosed in the following claims.

We claim:

1. An *Agkistrodon actus* antithrombosis enzyme having the following characteristics:
   the molecular weight of said enzyme is between about 28 kD and about 32 kD when analyzed by polyacrylamide gel electrophoresis,
   the aspartic acid content of said enzyme is between 2 and about 5%, with respect to percentage of total residues, and
   the glutamic acid content of said enzyme is between about 2% and about 5%, with respect to percentage of total residues, and said enzyme hydrolyzes fibrin, dissolves blood clots, and prevents platelet aggregation.

2. The enzyme of claim 1 which inhibits human platelet aggregation induced by a fibrin agonist selected from the group consisting of ADP, epinephrine and thrombin.

3. The enzyme of claim 1, wherein said enzyme has no detectable hydrolysis effect on casein.

4. The enzyme of claim 1, wherein said enzyme comprises $Ca^{++}$.

5. The enzyme of claim 1, wherein the amino terminus of said enzyme is aspartic acid.

6. The enzyme of claim 1, comprising two polypeptide chains of about 14 kD to about 16 kD when analyzed by polyacrylamide gel electrophoresis.

7. The enzyme of claim 6, wherein one of said two polypeptide chains comprises an amino acid sequence, from left to right in the direction from the amino acid terminus to the carboxy terminus, represented by the formula, SEQ ID NO: 3:
   Asp-Cys-Ser-Ser-Asp-Trp-Ser-Ser-Tyr-Glu-Gly-His-Cys-Tyr-Lys-Val-Phe-Lys-Gln-Ser-Lys-Thr-Trp-Thr-Asp-Ala-Glu-Ser-Phe-.

8. The enzyme of claim 6, wherein one of said two polypeptide chains comprises an amino acid sequence, from left to right in the direction from the amino terminus to the carboxy terminus, represented by the formula, SEQ ID NO: 4:
   Asp-Cys-Pro-Ser-Glu-trp-Ser-Ser-Tyr-Glu-Gly-Phe-Cys-Tyr-Lys-Pro-Phe-.

9. The enzyme of claim 6, wherein one of said two polypeptide chains comprises an amino acid sequence of SEQ ID NO: 2.

10. The enzyme of claim 1, which is crystallized.

11. An isolated, purified or recombinant *Agkistrodon actus* polypeptide, comprising; no less than 20 contiguous amino acids from SEQ ID NO: 2.

12. An isolated, purified or recombinant *Agkistrodon actus* polypeptide, comprising; SEQ ID NO: 2.

13. A pharmaceutical composition comprising a pharmaceutically effective amount of the enzyme of any of claims 1–12 and a pharmaceutically acceptable carrier.

* * * * *

```
                          SEQUENCE LISTING (1) GENERAL INFORMATION:

(iii) NUMBER OF SEQUENCES:      12

(2) INFORMATION FOR SEQ ID NO: 1:

(i) SEQUENCE CHARACTERISTICS:
         (A) LENGTH:          544 base pairs
         (B) TYPE:            nucleic acid
         (C) STRANDEDNESS:    single
         (D) TOPOLOGY:        linear (xi) SEQUENCE DESCRIPTION: SEQ ID NO: 1:

GAAGGGCATT GCTACAAGGT CTTCAAACAA TCTAAGACCT GGACAGATGC AGAGAGCTTC    60

TGCACGAAGC AGGTGAACGG GGGGCATCTG GTCTCTATCG AAAGCTCCGG AGAAGCAGAC   120

TTTGTGGGCC AGTTGATTGC TCAGAAGATA AAGTCAGCCA AAATCCATGT CTGGATCGGA   180

CTGAGGGCTC AAAACAAAGA AAAGCAATGC AGCATAGAGT GGAGCGATGG CTCCAGCATC   240

AGTTATGAGA ATTGGATTGA AGAAGAATCC AAAAAGTGTC TTGGGGTGCA CATAGAGACA   300

GGGTTTCATA AGTGGGAGAA TTTTTACTGT GAACAACAAG ATCCTTTTGT CTGCGAGGCA   360

TAGTCTGAAG ATCCAGCTGA TTGAAGTCTG GAGAAGCAAG GAAGCCCCCC ACCCCATCCC   420

CCAACCCTGC CTAGCCACAA TCTCTGCTAT GCACCCTTTG CTCAACGGAT GCTCTCTGTA   480

GCTGGATCTG GTGTTGCTGC TCCTGATGGG CCGGAAGTCA ATAAATTCTG CCTAGCCTGA   540

AAAA                                                                 544

(2) INFORMATION FOR SEQ ID NO: 2:

(i) SEQUENCE CHARACTERISTICS:
         (A) LENGTH:          129 amino acids
         (B) TYPE:            amino acid
         (C) STRANDEDNESS:    single
         (D) TOPOLOGY:        linear (ii) MOLECULE TYPE:        Peptide (xi) SEQUENCE DESCRIPTION: SEQ ID NO: 2:

Asp Cys Ser Ser Asp Trp Ser Ser Tyr Glu Gly His Cys Tyr Lys Val
 1               5                  10                  15

Phe Lys Gln Ser Lys Thr Trp Thr Asp Ala Glu Ser Phe Cys Thr Lys
                20                  25                  30

Gln Val Asn Gly Gly His Leu Val Ser Ile Glu Ser Ser Gly Glu Ala
            35                  40                  45

Asp Phe Val Gly Gln Leu Ile Ala Gln Lys Ile Lys Ser Ala Lys Ile
    50                  55                  60

His Val Trp Ile Gly Leu Arg Ala Gln Asn Lys Glu Lys Gln Cys Ser
65                  70                  75                  80

Ile Glu Trp Ser Asp Gly Ser Ser Ile Ser Lys Glu Asn Trp Ile Glu
                85                  90                  95
```

```
Glu Glu Ser Lys Lys Cys Leu Gly Val His Ile Glu Thr Gly Phe His
            100                 105                 110
Lys Trp Glu Asn Phe Tyr Cys Glu Gln Gln Asp Pro Phe Val Cys Glu
            115                 120                 125
Ala
```

(2) INFORMATION FOR SEQ ID NO: 3:

(i) SEQUENCE CHARACTERISTICS:
        (A) LENGTH:        29 amino acids
        (B) TYPE:          amino acid
        (C) STRANDEDNESS:  single
        (D) TOPOLOGY:     linear (ii) MOLECULE TYPE:     Peptide (xi) SEQUENCE DESCRIPTION: SEQ ID NO: 3:

```
Asp Cys Ser Ser Asp Trp Ser Ser Tyr Glu Gly His Cys Tyr Lys Val
 1               5                  10                  15
Phe Lys Gln Ser Lys Thr Trp Thr Asp Ala Glu Ser Phe
                20                  25
```

(2) INFORMATION FOR SEQ ID NO: 4:

(i) SEQUENCE CHARACTERISTICS:
        (A) LENGTH:        17 amino acids
        (B) TYPE:          amino acid
        (C) STRANDEDNESS:  single
        (D) TOPOLOGY:     linear (ii) MOLECULE TYPE:     Peptide (xi) SEQUENCE DESCRIPTION: SEQ ID NO: 4:

```
Asp Cys Pro Ser Glu Trp Ser Ser Tyr Glu Gly Phe Cys Tyr Lys Pro
 1               5                  10                  15
Phe
```

(2) INFORMATION FOR SEQ ID NO: 5:

(i) SEQUENCE CHARACTERISTICS:
        (A) LENGTH:        23 amino acids
        (B) TYPE:          amino acid
        (C) STRANDEDNESS:  single
        (D) TOPOLOGY:     linear (ii) MOLECULE TYPE:     Peptide (xi) SEQUENCE DESCRIPTION: SEQ ID NO: 5:

```
Met Gly Arg Phe Ile Phe Val Ser Phe Gly Leu Leu Val Val Phe Leu
 1               5                  10                  15
Ser Leu Ser Gly Thr Ala Ala
                20
```

(2) INFORMATION FOR SEQ ID NO: 6:

(i) SEQUENCE CHARACTERISTICS:
        (A) LENGTH:        6 amino acids
        (B) TYPE:          amino acid
        (C) STRANDEDNESS:  single
        (D) TOPOLOGY:     linear (ii) MOLECULE TYPE:     Peptide (xi) SEQUENCE DESCRIPTION: SEQ ID NO: 6:

```
Tyr Glu Gly His Cys Tyr
 1               5
```

(2) INFORMATION FOR SEQ ID NO: 7:

(i) SEQUENCE CHARACTERISTICS:
        (A) LENGTH:        20 base pairs
        (B) TYPE:          nucleic acid
        (C) STRANDEDNESS:  single
        (D) TOPOLOGY:      linear (xi) SEQUENCE DESCRIPTION: SEQ ID NO: 7:

TATGAAGGGC ATTGCTACAA                                                  20

(2) INFORMATION FOR SEQ ID NO: 8:

(i) SEQUENCE CHARACTERISTICS:
        (A) LENGTH:        20 base pairs
        (B) TYPE:          nucleic acid
        (C) STRANDEDNESS:  single
        (D) TOPOLOGY:      linear (xi) SEQUENCE DESCRIPTION: SEQ ID NO: 8:

CCATGGGGCG ATTCATCTTC                                                  20

(2) INFORMATION FOR SEQ ID NO: 9:

(i) SEQUENCE CHARACTERISTICS:
        (A) LENGTH:        19 base pairs
        (B) TYPE:          nucleic acid
        (C) STRANDEDNESS:  single
        (D) TOPOLOGY:      linear (xi) SEQUENCE DESCRIPTION: SEQ ID NO: 9:

CAGCTGCATC TTCAGACTA                                                   19

(2) INFORMATION FOR SEQ ID NO: 10:

(i) SEQUENCE CHARACTERISTICS:
        (A) LENGTH:        24 base pairs
        (B) TYPE:          nucleic acid
        (C) STRANDEDNESS:  single
        (D) TOPOLOGY:      linear (xi) SEQUENCE DESCRIPTION: SEQ ID NO: 10:

GGTGGCGACG ACTCCTGGAG CCCG                                       24

(2) INFORMATION FOR SEQ ID NO: 11:

(i) SEQUENCE CHARACTERISTICS:
        (A) LENGTH:        24 base pairs
        (B) TYPE:          nucleic acid
        (C) STRANDEDNESS:  single
        (D) TOPOLOGY:      linear (xi) SEQUENCE DESCRIPTION: SEQ ID NO: 11:

TTGACACCAG ACCAACTGGT AATG                                       24

(2) INFORMATION FOR SEQ ID NO: 12:

(i) SEQUENCE CHARACTERISTICS:
        (A) LENGTH:        454 base pairs
        (B) TYPE:          nucleic acid
        (C) STRANDEDNESS:  single
        (D) TOPOLOGY:      linear (ix) FEATURE:
        (A) NAME/KEY:      Coding Sequence
        (B) LOCATION:      3...440

-continued (D) OTHER INFORMATION: "N" stands for any base.
                      "Xaa" stands for any amino acid.

(xi) SEQUENCE DESCRIPTION: SEQ ID NO: 12:

```
CC ATG GGG CGA TTC ATC TTC GTG AGC TTC GGC TTG CTG GTC GTG TTC          47
   Met Gly Arg Phe Ile Phe Val Ser Phe Gly Leu Leu Val Val Phe
   1               5                   10                  15

CTC TCC CTG AGT GGA ACT GCA GCT GAT TGT CCC TCT GAG TGG TCC TCC         95
Leu Ser Leu Ser Gly Thr Ala Ala Asp Cys Pro Ser Glu Trp Ser Ser
                20                  25                  30

TAT GAA GGG CAT TGC TAC AAG CCC TTC GAT GAA CCT AAG ACC TGG GCA        143
Tyr Glu Gly His Cys Tyr Lys Pro Phe Asp Glu Pro Lys Thr Trp Ala
                35                  40                  45

GAT GCA GAG AAA TTC TGC ACA CAA CAA CAC AAA GGC AGC CAT CTG CCT        191
Asp Ala Glu Lys Phe Cys Thr Gln Gln His Lys Gly Ser His Leu Pro
        50                  55                  60

CTC ACA GCA GTG AGA GCG ATT GTG TNN NNN NNN NNT GGT CAC GTT GAC        239
Leu Thr Ala Val Arg Ala Ile Val Xaa Xaa Xaa Xaa Gly His Val Asp
        65                  70                  75

CAC ACC AAG TTG AAA CTG ATT AGT CTG ATT GGA CTG AAG AAC ATC TGG        287
His Thr Lys Leu Lys Leu Ile Ser Leu Ile Gly Leu Lys Asn Ile Trp
80                  85                  90                  95

AAC GGA TGC TAC TGG AAG TGG AGC GAT GGC ACC AAG CTC GAC TAC AAA        335
Asn Gly Cys Tyr Trp Lys Trp Ser Asp Gly Thr Lys Leu Asp Tyr Lys
                100                 105                 110

GAC TGG CGT GAA CAA TTT GAA TGT CTC GTA TCC AGG ACA GTT AAT AAC        383
Asp Trp Arg Glu Gln Phe Glu Cys Leu Val Ser Arg Thr Val Asn Asn
                115                 120                 125

GAA TGG CTA AGT ATG GAC TGC GGC ACT ACT TGC TCT TTC GTC TGC AAG        431
Glu Trp Leu Ser Met Asp Cys Gly Thr Thr Cys Ser Phe Val Cys Lys
        130                 135                 140

TTC CAG GCA TAGTCTGAAG ACTA                                            454
145
```